US012649161B2

(12) United States Patent
Zuo et al.

(10) Patent No.: US 12,649,161 B2
(45) Date of Patent: Jun. 9, 2026

(54) CONTROL METHOD AND APPARATUS FOR VAPORIZATION AMOUNT, AND VAPORIZATION APPARATUS

(71) Applicant: Shenzhen Moore Vaporization Health & Medical Technology Co., Ltd., Shenzhen (CN)

(72) Inventors: Zhaolin Zuo, Shenzhen (CN); Zhonghua Tan, Shenzhen (CN)

(73) Assignee: Shenzhen Moore Vaporization Health & Medical Technology Co., Ltd., Shenzhen (CN)

( * ) Notice: Subject to any disclaimer, the term of this patent is extended or adjusted under 35 U.S.C. 154(b) by 837 days.

(21) Appl. No.: 18/078,315

(22) Filed: Dec. 9, 2022

(65) Prior Publication Data

US 2023/0182158 A1 Jun. 15, 2023

(30) Foreign Application Priority Data

Dec. 15, 2021 (CN) .......................... 202111537184.1

(51) Int. Cl.
B05B 12/12 (2006.01)

(52) U.S. Cl.
CPC ... B05B 12/124 (2013.01); *A61M 2205/3372* (2013.01)

(58) Field of Classification Search
CPC .............. B05B 12/124; B05B 17/0646; A61M 2205/3372; A61M 11/00; A61M 35/00;
(Continued)

(56) References Cited

U.S. PATENT DOCUMENTS 4,714,635 A * 12/1987 Mochizuki ............ B05B 12/124
427/427.2
10,010,704 B2 * 7/2018 Hyde .................... A61M 35/25
(Continued)

FOREIGN PATENT DOCUMENTS

CN 108030946 A 5/2018
CN 208064337 U * 11/2018
(Continued)

OTHER PUBLICATIONS

Japanese Patent Office, Notice of Reasons for Refusal in Japanese Patent Application No. 2022-188215 (May 7, 2024).
(Continued)

*Primary Examiner* — Yongjia Pan
(74) *Attorney, Agent, or Firm* — Leydig, Voit & Mayer, Ltd.

(57) ABSTRACT

A control method for a vaporization amount includes: obtaining a vaporization distance between a vaporization apparatus and a vaporization object; determining a target vaporization power according to the vaporization distance, such that, if the vaporization distance is greater than or equal to a first threshold, the target vaporization power is a maximum vaporization power of the vaporization apparatus, and if the vaporization distance is less than the first threshold, the target vaporization power is determined according to a positive correlation between the vaporization distance and a vaporization power; and controlling a power of the vaporization apparatus according to the target vaporization power to adjust a vaporization amount of the vaporization apparatus.

9 Claims, 5 Drawing Sheets

(58) Field of Classification Search

CPC ......... A61M 2205/33; A45D 2200/057; A45D 34/00; Y02B 30/70; A24F 40/50; A24F 40/10; H02J 7/00712

See application file for complete search history.

(56) References Cited

U.S. PATENT DOCUMENTS

| | | | |
|---|---|---|---|
| 10,405,638 | B2 | 9/2019 | Streeter et al. |
| 10,775,128 | B2 * | 9/2020 | Thomann .............. F41B 9/0087 |
| 2006/0118039 | A1 * | 6/2006 | Cooper ................... B05B 12/12 |
| | | | 118/696 |
| 2009/0045270 | A1 | 2/2009 | Muljono |
| 2009/0179081 | A1 * | 7/2009 | Charpie ................ B05B 12/124 |
| | | | 239/289 |
| 2013/0296811 | A1 * | 11/2013 | Bangera ............. A61B 18/0218 |
| | | | 604/290 |
| 2014/0312141 | A1 * | 10/2014 | Ravishankar ........... B05B 12/12 |
| | | | 239/71 |
| 2018/0169682 | A1 | 6/2018 | Miller et al. |
| 2018/0177957 | A1 | 6/2018 | Streeter et al. |
| 2018/0193864 | A1 * | 7/2018 | Plantard ................ B05B 12/122 |
| 2019/0314598 | A1 | 10/2019 | Koerber et al. |

FOREIGN PATENT DOCUMENTS

| | | | | |
|---|---|---|---|---|
| CN | 210960810 | U | 7/2020 | |
| CN | 108714496 | B * | 1/2021 | ............. B05B 5/081 |
| CN | 108816542 | B * | 1/2021 | ............. B05B 5/006 |
| CN | 112546272 | A | 3/2021 | |
| CN | 113615895 | A * | 11/2021 | ............. A24F 40/51 |
| EP | 0212442 | B1 * | 11/1990 | ........... B05B 7/0815 |
| EP | 3375323 | B1 | 9/2021 | |
| FR | 3053233 | A1 * | 1/2018 | .......... B05B 12/002 |
| JP | S6233572 | A * | 2/1987 | |
| JP | 2002011386 | A * | 1/2002 | .............. B05B 5/10 |
| JP | 3106462 | U | 1/2005 | |
| JP | 201173617 | A | 4/2011 | |
| JP | 2011073617 | A * | 4/2011 | .............. B60H 3/02 |
| JP | 201266047 | A | 4/2012 | |
| JP | 2015230108 | A | 12/2015 | |
| JP | 2020501896 | A | 1/2020 | |
| KR | 930001503 | B1 * | 3/1993 | .......... B05B 7/0815 |
| WO | 2009091489 | A1 | 7/2009 | |
| WO | 2018043735 | A1 | 3/2018 | |
| WO | 2018118715 | A1 | 6/2018 | |

OTHER PUBLICATIONS

Chinese Patent Office, Office Action in Chinese Patent Application No. 202111537184.1 (Mar. 24, 2025).

Korean Patent Office, Office Action in Korean Patent Application No. 10-2022-0154430 (Apr. 1, 2025).

Korean Patent Office, Notice of Allowance in Korean Patent Application No. 10-2022-0154430 (Jun. 5, 2025).

European Patent Office, Intention to grant in European Patent Application No. 22213469.4 (May 12, 2025).

European Patent Office, Search Report in European Patent Application No. 22213469.4 (May 19, 2023).

Japanese Patent Office, Notice of Reasons for Refusal in Japanese Patent Application No. 2022-188215 (Nov. 7, 2023).

Chinese Patent Office, Notification of grant of patent right for invention in Chinese Patent Application No. 202111537184.1 (Aug. 29, 2025).

* cited by examiner

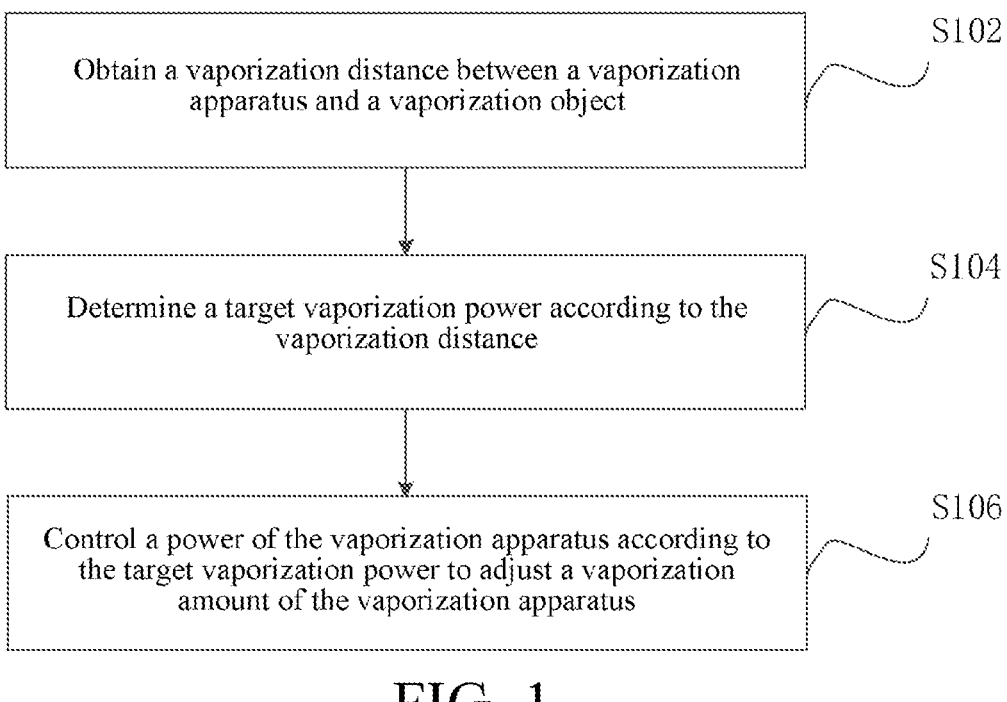

```
┌─────────────────────────────────────────────────┐        S102
│   Obtain a vaporization distance between a        │       ⌇
│   vaporization apparatus and a vaporization       │
│                 object                            │
└─────────────────────────────────────────────────┘
                         │
                         ▼
┌─────────────────────────────────────────────────┐        S104
│   Determine a target vaporization power           │       ⌇
│   according to the vaporization distance          │
└─────────────────────────────────────────────────┘
                         │
                         ▼
┌─────────────────────────────────────────────────┐        S106
│   Control a power of the vaporization apparatus   │       ⌇
│   according to the target vaporization power to   │
│   adjust a vaporization amount of the             │
│   vaporization apparatus                          │
└─────────────────────────────────────────────────┘
```

FIG. 1

```
┌─────────────────────────────────────────────────┐        S202
│                                                   │       ⌇
│        Obtain an influence vaporization           │
│                 parameter                         │
│                                                   │
└─────────────────────────────────────────────────┘
                         │
                         ▼
┌─────────────────────────────────────────────────┐        S204
│     Select a curve corresponding to the           │       ⌇
│  influence vaporization parameter from a          │
│  plurality of to-be-selected curves as a          │
│              control curve                        │
└─────────────────────────────────────────────────┘
```

FIG. 2

CONTROL METHOD AND APPARATUS FOR VAPORIZATION AMOUNT, AND VAPORIZATION APPARATUS

CROSS-REFERENCE TO PRIOR APPLICATION

Priority is claimed to Chinese Patent Application No. 202111537184.1, filed on Dec. 15, 2021, the entire disclosure of which is hereby incorporated by reference herein.

FIELD

This application relates to the field of vaporization amount control technologies, and in particular, to a control method and apparatus for a vaporization amount, a vaporization apparatus, and a computer-readable storage medium.

BACKGROUND

As people pay more attention to the maintenance of personal skin, vaporization apparatuses are gradually widely applied to skin care and maintenance. The vaporization apparatus generates an aerosol by vaporizing a vaporization medium, and sprays the aerosol on the skin of a vaporization object, so as to implement the skin care and maintenance.

The vaporization apparatus in the conventional art has the problem of being difficult to precisely control vaporization amount, which leads to a problem of fluid accumulation on the skin of a user due to an excessive amount of aerosol, or a problem of failing to bring the aerosol into contact with the skin of the user due to an excessively small amount of aerosol.

SUMMARY

In an embodiment, the present invention provides a control method for a vaporization amount, the control method comprising: obtaining a vaporization distance between a vaporization apparatus and a vaporization object; determining a target vaporization power according to the vaporization distance, such that, if the vaporization distance is greater than or equal to a first threshold, the target vaporization power comprises a maximum vaporization power of the vaporization apparatus, and if the vaporization distance is less than the first threshold, the target vaporization power is determined according to a positive correlation between the vaporization distance and a vaporization power; and controlling a power of the vaporization apparatus according to the target vaporization power to adjust a vaporization amount of the vaporization apparatus.

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following:

FIG. 1 is a schematic flowchart of a control method for a vaporization amount in an embodiment;

FIG. 2 is a schematic flowchart of obtaining a control curve in an embodiment;

DETAILED DESCRIPTION

Figure 3:
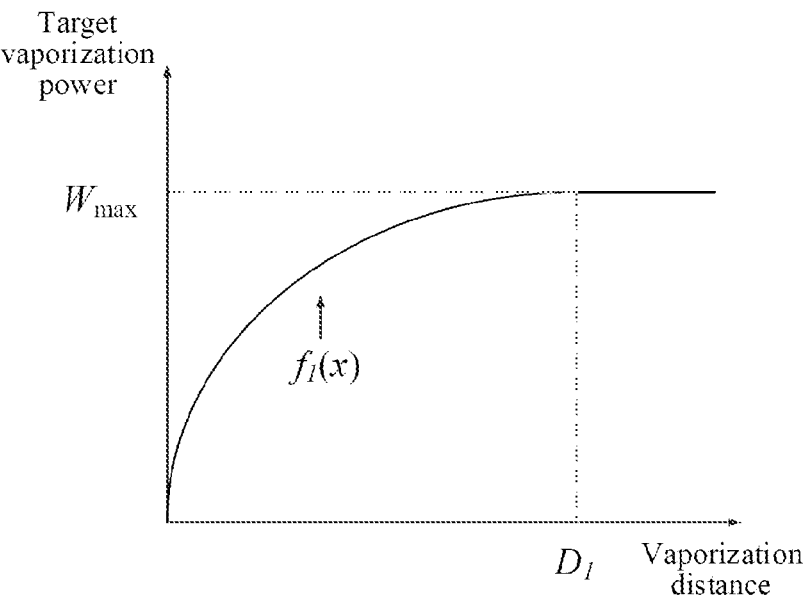
FIG. 3 is a schematic diagram of a first control curve in an embodiment.

In an embodiment, the present invention provides a control method and apparatus for a vaporization amount, a vaporization apparatus, and a computer-readable storage medium to precisely adjust the vaporization amount.

According to one aspect, an embodiment of the present invention provides a control method for a vaporization amount, the control method including: obtaining a vaporization distance between a vaporization apparatus and a vaporization object; determining a target vaporization power according to the vaporization distance, where in a case that the vaporization distance is greater than or equal to a first threshold, the target vaporization power is a maximum vaporization power of the vaporization apparatus, and in a case that the vaporization distance is less than the first threshold, the target vaporization power is determined according to a positive correlation between the vaporization distance and a vaporization power; and controlling a power of the vaporization apparatus according to the target vaporization power to adjust a vaporization amount of the vaporization apparatus.

In an embodiment, before the step of determining a target vaporization power according to the vaporization distance, the control method further includes: obtaining an influence vaporization parameter, the influence vaporization parameter including an environmental parameter and/or a vaporization medium type; and selecting a curve corresponding to the influence vaporization parameter from a plurality of to-be-selected curves as a control curve, where the control curve is used to obtain a target vaporization power according to the vaporization distance.

In an embodiment, the control curve includes a first control curve, and the first control curve is as follows:

$$y(x) = \begin{cases} f_1(x), & x < D_1 \\ W_{max}, & x \ge D_1 \end{cases}$$

In the formula, x is the vaporization distance, y(x) is the target vaporization power corresponding to the vaporization distance, $D_1$ is the first threshold, Wmax is the maximum vaporization power, $f1(x)$ reflects the positive correlation between the vaporization distance and the vaporization power, and a slope of $f1(x)$ decreases with the increase of the vaporization distance.

In an embodiment, the control curve includes a second control curve, and the second control curve is as follows:

$$y(x) = \begin{cases} f_2(x), & x < D_1 \\ W_{max}, & x \ge D_1 \end{cases}$$

In the formula, x is the vaporization distance, y(x) is the target vaporization power corresponding to the vaporization distance, $D_1$ is the first threshold, Wmax is the maximum vaporization power, $f2(x)$ reflects the positive correlation between the vaporization distance and the vaporization power, and a slope of $f2(x)$ remains unchanged.

In an embodiment, the control method further includes: sending a prompt signal in a case that the target vaporization power is the maximum vaporization power.

In an embodiment, the step of controlling a power of the vaporization apparatus according to the target vaporization power further includes: turning off the vaporization apparatus if the vaporization distance is greater than the first threshold within a preset duration.

In an embodiment, the vaporization apparatus includes a vaporization unit and a drive unit, the drive unit is configured to output a drive signal, and the vaporization unit is configured to vaporize a vaporization medium according to the drive signal; and the step of controlling a power of the vaporization apparatus according to the target vaporization power includes: outputting a control signal to the drive unit according to the target vaporization power, the control signal being used to adjust the drive signal to adjust a power of the vaporization unit.

According to another aspect, an embodiment of the present invention further provides a vaporization apparatus, including: a vaporization unit, configured to vaporize a vaporization medium; a ranging unit, configured to detect a vaporization distance between the vaporization apparatus and a vaporization object; and a controller, configured to control a power of the vaporization unit to adjust a vaporization amount of the vaporization apparatus, and including a memory and a processor, the memory storing a computer program, and the computer program, when executed by the processor, implementing the steps of the control method for a vaporization amount according to any one of the above embodiments.

According to another aspect, an embodiment of the present invention provides a control apparatus for a vaporization amount, the control apparatus including: a distance obtaining module, configured to obtain a vaporization distance between a vaporization apparatus and a vaporization object; a target vaporization power determination module, configured to determine a target vaporization power according to the vaporization distance, where in a case that the vaporization distance is greater than or equal to a first threshold, the target vaporization power is a maximum vaporization power of the vaporization apparatus, and in a case that the vaporization distance is less than the first threshold, the target vaporization power is determined according to a positive correlation between the vaporization distance and a vaporization power; and an adjustment module, configured to control a power of the vaporization apparatus according to the target vaporization power to adjust a vaporization amount of the vaporization apparatus.

According to another aspect, an embodiment of the present invention provides a computer-readable storage medium, storing a computer program, the computer program, when executed by a processor, implementing the steps of the control method for a vaporization amount according to any one of the above embodiments.

Based on any of the above embodiments, in a case that the vaporization distance is less than the first threshold, the vaporization amount is adaptively adjusted by increasing the power of the vaporization apparatus, so as to ensure that the aerosol can effectively act on the vaporization object, and avoid the problem of liquid accumulation due to an excessively close distance to the vaporization object or the problem of failing to bring the aerosol into contact with the vaporization object due to an excessively far distance to the object. In a case that the vaporization distance is greater than or equal to the first threshold, the vaporization apparatus is maintained to operate at the maximum vaporization power, so that the waste of the vaporization medium and energy can be avoided, to save energy and the usage amount of the vaporization medium.

For ease of understanding this application, this application is described more comprehensively below with reference to the accompanying drawings. The accompanying drawings show embodiments of this application. However, this application may be implemented in many different forms, and is not limited to the embodiments described in this specification. On the contrary, the embodiments are provided to make the disclosed content of this application more thorough and comprehensive.

Unless otherwise defined, meanings of all technical and scientific terms used in this specification are the same as those usually understood by a person skilled in the art to which this application belongs. In this application, terms used in the specification of this application are merely intended to describe objectives of the specific embodiments, but are not intended to limit this application.

It may be understood that the terms "first", "second", and the like used in this application may be used for describing various elements in this specification. However, the elements are not limited by the terms. The terms are merely used for distinguishing a first element from another element.

Spatial relationship terms such as "under", "beneath", "lower", "below", "above", and "upper" may be used here to describe a relationship between one element or feature and the other elements or features shown in the drawings. It should be understood that in addition to the orientation shown in the drawings, the spatial relationship term further includes different orientations of the devices in use and operation. For example, if the device in the drawings is flipped, an element or a feature described as "beneath the other elements", "below the other elements", or "under the other elements" is oriented "above" the other elements or features. Therefore, the exemplary terms "beneath" and "under" may include both orientations of above and below. In addition, the device may also include an additional orientation (for example, rotation of 90 degrees, or other orientations), and spatial descriptors used herein are interpreted accordingly.

It should be noted that when an element is considered to be "connected" to another element, the element may be directly connected to the another element, or may be connected to the another element by a central element. In addition, the "connection" in the following embodiments should be understood as "electrical connection", "communication connection" and the like if there is a transmission of electrical signals or data between the objects to be connected.

As used herein, the singular forms "a", "an", and "/the" may also include the plural forms, unless the context clearly indicates otherwise. It should further be understood that the term "comprise/include", "have", or the like specifies the presence of stated features, integers, steps, operations, components, parts, or combinations thereof, but does not exclude the possibility of the presence or addition of one or more other features, integers, steps, operations, components, parts, or combinations thereof. In addition, the term "and/or" as used in this specification includes any of the items listed therein and all combinations thereof.

As mentioned in the BACKGROUND section, the vaporization apparatus in the prior art has the problem of being difficult to precisely control the vaporization amount. The inventors have found that the cause to this problem is that the vaporization amount of the existing vaporization apparatus is often a fixed value, such as a vaporization cosmetic apparatus and a vaporization care apparatus. When a user is close to the vaporization apparatus, the vaporization amount is excessively large, which causes liquid accumulation of the aerosol on the skin of the user. When the user is far away from the vaporization apparatus, the vaporization amount is excessively small, which causes the failure in bringing the aerosol into contact with the skin of the user.

Based on the above problem, an embodiment of the present invention provides a control method for a vaporization amount. Referring to FIG. 1, the control method includes steps S102 to S106.

S102: Obtain a vaporization distance between a vaporization apparatus and a vaporization object.

It may be understood that the vaporization object refers to an action object of the vaporization apparatus, which may be the skin such as the hand and the face of the user. Since the problem in the BACKGROUND section is caused by the fact that the vaporization amount is not adjusted as the vaporization distance changes, the vaporization distance needs to be obtained first and then the vaporization amount can be adaptively adjusted for the vaporization distance. Optionally, the vaporization distance can be obtained by a ranging sensor, such as an ultrasonic ranging sensor or an infrared ranging sensor. A precise vaporization distance is obtained for different parts requiring vaporization of the user, and an image acquisition apparatus and a position adjustment apparatus may be disposed on the vaporization apparatus. The position adjustment apparatus is configured to adjust a ranging direction of the ranging sensor. The image acquisition apparatus is configured to acquire a user image. The user image is acquired by the image acquisition apparatus; image recognition processing is performed on the user image according to a part selection instruction to determine a position of a target part; and the position adjustment apparatus is controlled according to the position of the target part, so that the ranging sensor points to the target part. The user may send the part selection instruction to the vaporization apparatus by interacting with the vaporization apparatus.

S104: Determine a target vaporization power according to the vaporization distance.

In a case that the vaporization distance is greater than or equal to a first threshold, the target vaporization power is a maximum vaporization power of the vaporization apparatus, and in a case that the vaporization distance is less than the first threshold, the target vaporization power is determined according to a positive correlation between the vaporization distance and a vaporization power. It may be understood that the first threshold is the farthest vaporization distance at which the vaporization apparatus can effectively act on the vaporization object. Considering an upper limit of the vaporization power of the vaporization apparatus, the waste of energy due to the excessive vaporization power, and the fact that many aerosols are dissipated into the air and therefore the vaporization medium is not effectively utilized, in a case that the vaporization distance is above the first threshold, it is impossible to ensure that the aerosol effectively acts on the vaporization object by continuing to increase the power of the vaporization apparatus. In some embodiments, a prompt signal is sent in a case that the target vaporization power is the maximum vaporization power. Since it is difficult for the user to precisely perceive a distance between the user and the vaporization apparatus, the user may be notified by a prompt signal that a vaporization distance between the user and the vaporization apparatus is excessively far and the user needs to adjust the position. The prompt signal may be sent by a reminder unit disposed on the vaporization apparatus, and the reminder unit may be a buzzer, a vibration motor, and/or a LED light.

S106: Control a power of the vaporization apparatus according to the target vaporization power to adjust a vaporization amount of the vaporization apparatus.

Specifically, the vaporization apparatus includes a vaporization unit, the vaporization unit is configured to vaporize a vaporization medium, and a larger power of the vaporization unit indicates a larger vaporization amount of the vaporization apparatus. Therefore, the vaporization amount of the vaporization apparatus can be adjusted by changing the power of the vaporization unit. In addition, the above steps can be repeated for multiple times during the whole process of the user using the vaporization apparatus, to obtain the vaporization distance in real time and adjust the target vaporization power in real time, so as to implement dynamic adjustment of the vaporization amount.

Based on the control method for a vaporization amount in this embodiment, in a case that the vaporization distance is less than the first threshold, the vaporization amount is adaptively adjusted by increasing the power of the vaporization apparatus, so as to ensure that the aerosol can effectively act on the vaporization object, and avoid the problem of liquid accumulation due to an excessively close distance to the vaporization object or the problem of failing to bring the aerosol into contact with the vaporization object due to an excessively far distance to the object. In a case that the vaporization distance is greater than or equal to the first threshold, the vaporization apparatus is maintained to operate at the maximum vaporization power, so that the waste of the vaporization medium and energy can be avoided, to save energy and the usage amount of the vaporization medium.

In an embodiment, the step of controlling a power of the vaporization apparatus according to the target vaporization power further includes: turning off the vaporization apparatus if the vaporization distance is greater than the first threshold within a preset duration. It may be understood that if the vaporization distance is greater than the first threshold for a long time, it is difficult for the vaporization apparatus to effectively act on the user, which wastes energy and fails to achieve good effects. Therefore, when the case in this embodiment occurs, the effect of saving energy is achieved by turning off the vaporization apparatus. In a specific embodiment, the preset duration is 30 seconds.

In an embodiment, before the step of determining a target vaporization power according to the vaporization distance, the control method further includes step S202 and step S204.

S202: Obtain an influence vaporization parameter.

The influence vaporization parameter includes an environmental parameter and/or a vaporization medium type. Specifically, the environmental parameter may be a physical amount that affects a vaporization rate of the vaporization medium, such as temperature or moisture outside the vaporization apparatus. In addition, the power of the same vaporization apparatus and the vaporization rate of each vaporization medium under the same environmental parameter may be tested, and those with relatively similar vaporization rates may be classified into the same vaporization medium type. In combination with the above description, it can be seen that the vaporization rate of the vaporization medium is different when the power of the vaporization apparatus is the same and the influence vaporization parameter is different. The environmental parameter can be obtained by corresponding sensors such as a temperature sensor and a moisture sensor. Commonly used vaporization mediums can be classified according to the vaporization medium type and then attached to a product manual, so that the user can input the vaporization medium type to the vaporization apparatus by interacting with the vaporization apparatus. The vaporization mediums of different vaporization medium types contain specific chemical components, and therefore the composition of the vaporization medium can also be detected by disposing an electrochemical sensor in the vaporization apparatus, so that the vaporization apparatus automatically obtains the vaporization medium type. Taking the environmental parameter including temperature as an example, for a case of temperature T1>temperature T2, before the target vaporization power reaches the maximum vaporization power, a to-be-selected curve L1 corresponding to temperature T1 is higher than a to-be-selected curve L2 corresponding to temperature T2. That is, before the target vaporization power reaches the maximum vaporization power, for the same vaporization distance, a target vaporization power of the to-be-selected curve L1 is higher than a target vaporization power of the to-be-selected curve L2. Taking the environmental parameter including moisture as an example, for a case of moisture M1>moisture M2, before the target vaporization power reaches the maximum vaporization power, a to-be-selected curve L1 corresponding to moisture M1 is lower than a to-be-selected curve L2 corresponding to moisture M2. That is, before the target vaporization power reaches the maximum vaporization power, for the same vaporization distance, a target vaporization power of the to-be-selected curve L1 is lower than a target vaporization power of the to-be-selected curve L2.

S204: Select a curve corresponding to the influence vaporization parameter from a plurality of to-be-selected curves as a control curve.

The control curve is used to obtain a target vaporization power according to the vaporization distance. It may be understood that the control curve can reflect a one-to-one correspondence between the vaporization distance and the target vaporization power. In this embodiment, the determining of the target vaporization power according to the vaporization distance is implemented through the control curve. However, because the influence vaporization parameters are different when the user uses the vaporization apparatus, a plurality of to-be-selected curves can be stored in the vaporization apparatus, and each to-be-selected curve is obtained by experiment and analysis based on the corresponding influence vaporization parameter. After obtaining the influence vaporization parameter, the vaporization apparatus can select one from these to-be-selected curves as a control curve, so that the vaporization apparatus can accurately select the target vaporization power under various environments and vaporization medium types.

In an embodiment, the control curve includes a first control curve. Referring to FIG. 3, the first control curve is as follows:

$$y(x) = \begin{cases} f_1(x), x < D_1 \\ W_{max}, x \geq D_1 \end{cases}$$

In the formula, x is the vaporization distance, y(x) is the target vaporization power corresponding to the vaporization distance, D1 is the first threshold, Wmax is the maximum vaporization power, $f_1(x)$ reflects the positive correlation between the vaporization distance and the vaporization power, and a slope of $f_1(x)$ decreases with the increase of the vaporization distance. It may be understood that in a case that the vaporization distance is less than the first threshold, the target vaporization power increases non-linearly with the increase of the vaporization distance. When the vaporization distance is small, the target vaporization power is increased at a fast speed first, so that the user does not have the experience that the vaporization amount is excessively small at the beginning of use. Each to-be-selected curve may be similar in shape to the first control curve, except that the parameter of $f_1(x)$ and/or the first threshold in each to-be-selected curve is different, and the parameter in each $f_1(x)$ may be obtained by fitting experimental data. The fitting can be implemented through algorithms of a neural network and machine learning.

Figure 4:
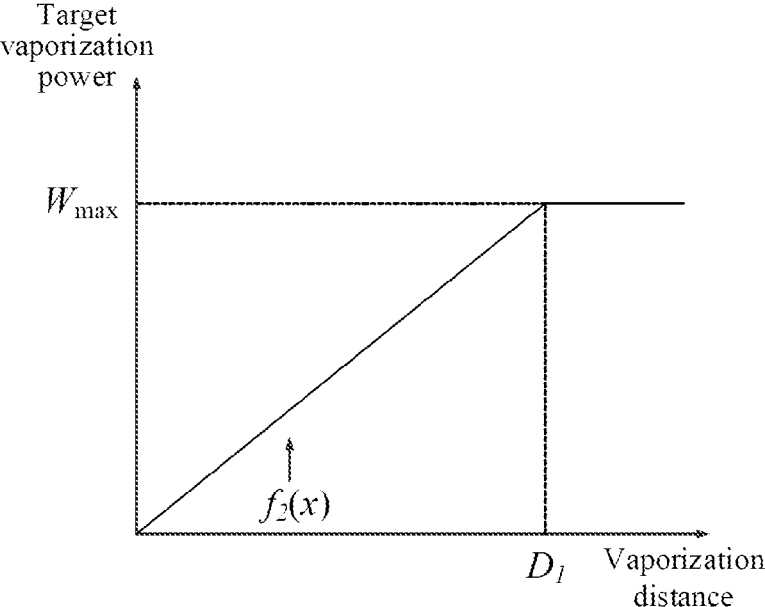
FIG. 4 is a schematic diagram of a second control curve in an embodiment.

In an embodiment, the control curve includes a second control curve. Referring to FIG. 4, the second control curve is as follows:

$$y(x) = \begin{cases} f_2(x), x < D_1 \\ W_{max}, x \geq D_1 \end{cases}$$

In the formula, x is the vaporization distance, y(x) is the target vaporization power corresponding to the vaporization distance, D1 is the first threshold, Wmax is the maximum vaporization power, $f_2(x)$ reflects the positive correlation between the vaporization distance and the vaporization power, and a slope of $f_2(x)$ remains unchanged. It may be understood that in a case that the vaporization distance is less than the first threshold, the target vaporization power increases linearly with the increase of the vaporization distance, so that the vaporization amount changes uniformly with the change of the vaporization distance. Each to-be-selected curve may be similar in shape to the second control curve, except that the parameter of $f_2(x)$ and/or the first threshold in each to-be-selected curve is different, and the parameter in each $f_2(x)$ may be obtained by fitting experimental data.

In an embodiment, the vaporization apparatus includes a vaporization unit and a drive unit, the drive unit is configured to output a drive signal, and the vaporization unit is configured to vaporize a vaporization medium according to the drive signal. The step of controlling a power of the vaporization apparatus according to the target vaporization power includes: outputting a control signal to the drive unit according to the target vaporization power. The control signal is used to adjust the drive signal to adjust a power of the vaporization unit. It may be understood that a power supply of the vaporization apparatus outputs a drive signal to the vaporization unit through the drive unit, and changes the drive signal by changing the control signal, so that the power adjustment of a vaporization piece can be implemented.

It should be understood that, although each step of the flowcharts in FIG. 1 and FIG. 2 is displayed sequentially according to arrows, the steps are not necessarily performed according to an order indicated by arrows. Unless clearly specified in this specification, there is no strict sequence limitation on the execution of the steps, and the steps may be performed in another sequence. Moreover, at least some steps in FIG. 1 and FIG. 2 may include a plurality of steps or a plurality of stages. The steps or the stages are not necessarily performed at the same moment, but may be performed at different moments. The steps or the stages are not necessarily performed in sequence, but may be performed in turn or alternately with another step or at least some of steps or stages of the another step.

Figure 5:
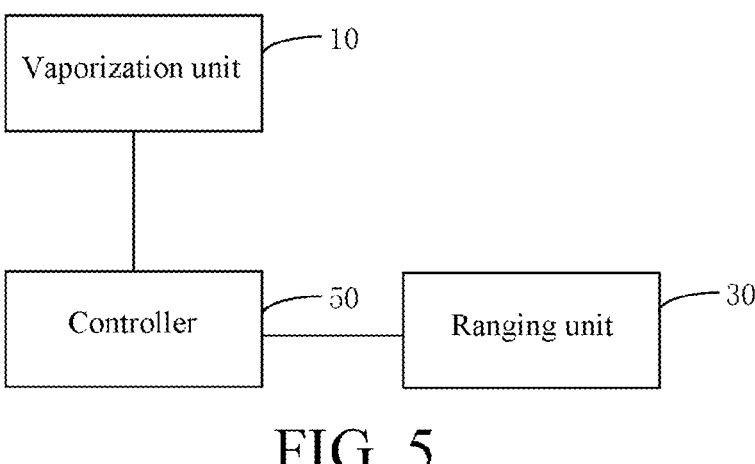
FIG. 5 is a structural block diagram of a vaporization apparatus in an embodiment.

An embodiment of the present invention further provides a vaporization apparatus. Referring to FIG. 5, the vaporization apparatus includes a vaporization unit 10, a ranging unit 30, and a controller 50. The vaporization unit 10 is configured to vaporize a vaporization medium. The vaporization unit 10 may be a vaporization unit 10 based on principles such as ultrasonic vaporization, mesh vaporization, or compression vaporization. The vaporization medium may be a mixture of water, various maintenance essential oils, maintenance lotions, and the like. The ranging unit 30 is configured to detect a vaporization distance between the vaporization apparatus and a vaporization object. In a specific embodiment, the ranging unit 30 includes an infrared ranging sensor, an ultrasonic ranging sensor, and/or a laser range sensor. The controller 50 is configured to control a power of a vaporization unit 10 to adjust a vaporization amount of the vaporization apparatus, and includes a memory and a processor, the memory storing a computer program, and the computer program, when executed by the processor, implementing: obtaining a vaporization distance between the vaporization apparatus and a vaporization object; determining a target vaporization power according to the vaporization distance, where in a case that the vaporization distance is greater than or equal to a first threshold, the target vaporization power is a maximum vaporization power of the vaporization apparatus, and in a case that the vaporization distance is less than the first threshold, the target vaporization power is determined according to a positive correlation between the vaporization distance and a vaporization power; and controlling a power of the vaporization apparatus according to the target vaporization power to adjust a vaporization amount of the vaporization apparatus.

Based on the vaporization apparatus in this embodiment, in a case that the vaporization distance is less than the first threshold, the vaporization amount is adaptively adjusted by increasing the power of the vaporization apparatus, so as to ensure that the aerosol can effectively act on the vaporization object, and avoid the problem of liquid accumulation due to an excessively close distance to the vaporization object or the problem of failing to bring the aerosol into contact with the vaporization object due to an excessively far distance to the object. In a case that the vaporization distance is greater than or equal to the first threshold, the vaporization apparatus is maintained to operate at the maximum vaporization power, so that the waste of the vaporization medium and energy can be avoided, to save energy and the usage amount of the vaporization medium.

In an embodiment, the controller 50 is further configured to implement the steps in any embodiment of the control method for a vaporization amount.

Figure 6:
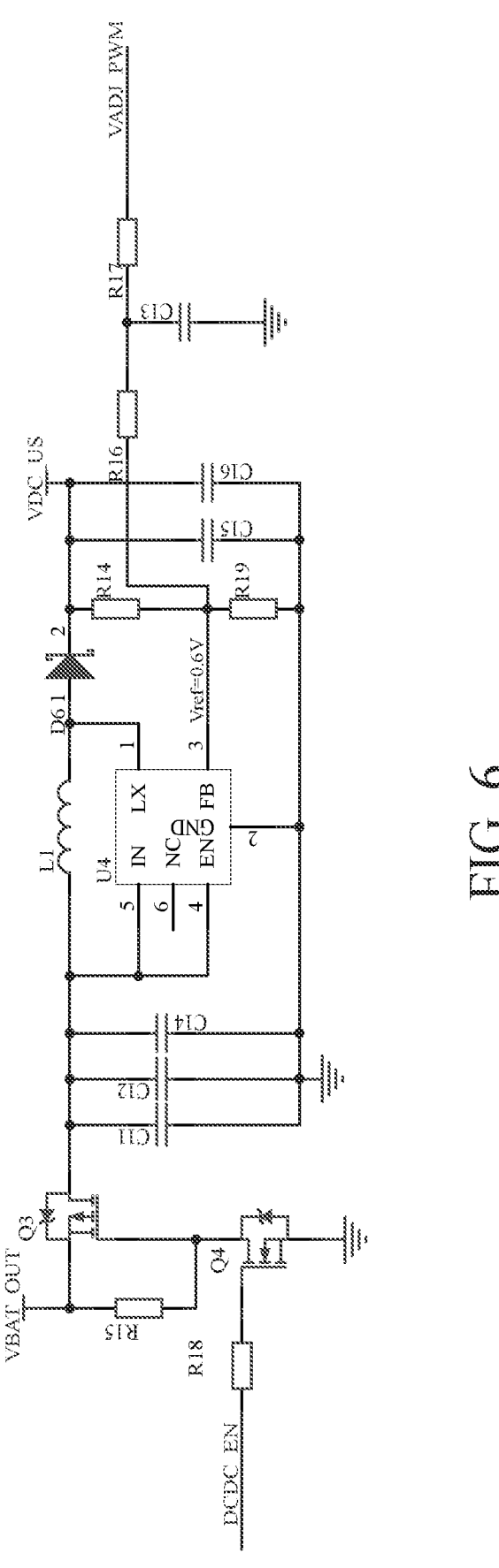
FIG. 6 is a schematic circuit diagram of a vaporization unit in an embodiment.

In an embodiment, the vaporization apparatus further includes a drive unit. The drive unit is configured to output a drive signal, and the vaporization unit 10 is configured to vaporize a vaporization medium according to the drive signal. In a specific embodiment, referring to FIG. 6, the drive unit includes a boost chip U4. A DCDC_EN pin of the controller 50 is connected to a control end of a switch transistor Q4 through a resistor R18, a source of the switch transistor Q4 is grounded, and a drain of the switch transistor Q4 is respectively connected to a control end of a switch transistor Q3, and connected to a power supply VBAT_OUT of the vaporization apparatus through a resistor R15. A source of the switch transistor Q3 is connected to the VBAT_OUT, and a drain of the switch transistor Q3 is grounded through a capacitor C11, a capacitor C12, and a capacitor C14, respectively. The drain of the switch transistor Q3 is further connected to an input pin IN and an enable pin EN of the boost chip U4, and the drain of the switch transistor Q3 is further connected to an LX pin of the boost chip U4 through an inductor L1. A GND pin of the boost chip U4 is grounded, and the LX pin of the boost chip U4 is connected to an input end of a Schottky diode D1. An output end of the Schottky diode D1 is grounded through a resistor R14 and a resistor R19 in sequence, and is grounded through a capacitor C15 and a capacitor C16 respectively. The output end of the Schottky diode D1 outputs a drive signal to the vaporization unit 10 through a resistor R20. A VDAJ_PWM pin of the controller 50 is connected to common ends of the resistor R14 and the resistor R19 through a resistor R17 and a resistor R16 in sequence, and then connected to a feedback pin FB of the boost chip U4 through the common ends of the resistor R14 and the resistor R19. Common ends of the resistor R17 and the resistor R16 are further grounded through a capacitor C13.

An operation principle of the above circuit is as follows: The controller 50 enables the boost chip U4 through the DCDC_EN pin, and then changes a drive signal outputted from the boost chip U4 by adjusting a control signal outputted from the VADJ_PWM pin. The controller 50 obtains a voltage and a current of the drive signal by connecting an ADC sampling pin to two ends of the resistor R20, so as to calculate a real-time power of the vaporization unit 10 and determine whether the vaporization unit 10 reaches the target vaporization power according to the real-time power of the vaporization unit 10.

Figure 7:
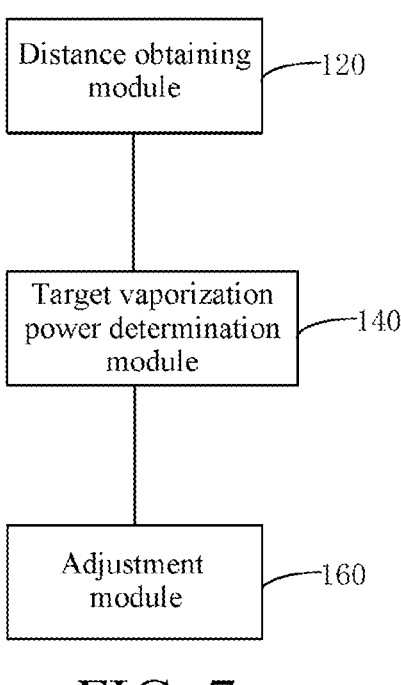
FIG. 7 is a structural block diagram of a control apparatus for a vaporization amount in an embodiment.

Referring to FIG. 7, an embodiment of the present invention provides a control apparatus for a vaporization amount, and the control apparatus includes a distance obtaining module 120, a target vaporization power determination module 140, and an adjustment module 160. The distance obtaining module 120 is configured to obtain a vaporization distance between a vaporization apparatus and a vaporization object. The target vaporization power determination module 140 is configured to determine a target vaporization power according to the vaporization distance. In a case that the vaporization distance is greater than or equal to a first threshold, the target vaporization power is a maximum vaporization power of the vaporization apparatus, and in a case that the vaporization distance is less than the first threshold, the target vaporization power is determined according to a positive correlation between the vaporization distance and a vaporization power. The adjustment module 160 is configured to control a power of the vaporization apparatus according to the target vaporization power to adjust a vaporization amount of the vaporization apparatus.

Based on the control apparatus for a vaporization amount in this embodiment, in a case that the vaporization distance is less than the first threshold, the vaporization amount is adaptively adjusted by increasing the power of the vaporization apparatus, so as to ensure that the aerosol can effectively act on the vaporization object, and avoid the problem of liquid accumulation due to an excessively close distance to the vaporization object or the problem of failing to bring the aerosol into contact with the vaporization object due to an excessively far distance to the object. In a case that the vaporization distance is greater than or equal to the first threshold, the vaporization apparatus is maintained to operate at the maximum vaporization power, so that the waste of the vaporization medium and energy can be avoided, to save energy and the usage amount of the vaporization medium.

In an embodiment, the control apparatus for a vaporization amount further includes a control curve obtaining module. The control curve obtaining module includes an influence vaporization parameter obtaining unit and a curve selection unit. The influence vaporization parameter obtaining unit is configured to obtain an influence vaporization parameter. The influence vaporization parameter includes an environmental parameter and/or a vaporization medium type. The curve selection unit is configured to select a curve corresponding to the influence vaporization parameter from a plurality of to-be-selected curves as a control curve. The control curve is used to obtain a target vaporization power according to the vaporization distance.

In an embodiment, the vaporization apparatus includes a vaporization unit 10 and a drive unit, the drive unit is configured to output a drive signal, and the vaporization unit 10 is configured to vaporize a vaporization medium according to the drive signal. The adjustment module 160 is configured to output a control signal to the drive unit according to the target vaporization power. The control signal is used to adjust the drive signal to adjust a power of the vaporization unit 10.

In an embodiment, the control apparatus for a vaporization amount further includes a prompt module. The prompt module is configured to send a prompt signal in a case that the target vaporization power is the maximum vaporization power.

In an embodiment, the control apparatus for a vaporization amount further includes a shutdown module. The shutdown module is configured to turn off the vaporization apparatus if the vaporization distance is greater than the first threshold within a preset duration.

For a specific limitation on the control apparatus for a vaporization amount, reference may be made to the limitation on the control method for a vaporization amount above. Details are not described herein again. All or some of the foregoing modules in the control apparatus for a vaporization amount may be implemented by software, hardware, or a combination thereof. The foregoing modules may be built in or independent of a processor of a computer device in a hardware form, or may be stored in a memory of the computer device in a software form, so that the processor invokes and performs an operation corresponding to each of the foregoing modules. It should be noted that module division in the embodiments of this application is an example, and is only logical function division. In an actual implementation, there may be another division manner.

According to another aspect, an embodiment of the present invention provides a computer-readable storage medium, storing a computer program, the computer program, when executed by a processor, implementing the steps of the control method for a vaporization amount according to any one of the above embodiments.

A person of ordinary skill in the art may understand that some or all procedures in the foregoing method embodiments may be implemented by a computer program instructing related hardware. The computer program may be stored in a non-volatile computer-readable storage medium, and when the computer program is executed, the procedures of the foregoing method embodiments may be performed. Any reference to a memory, a storage, a database, or another medium used in the embodiments provided in this application may include at least one of a non-volatile memory and a volatile memory. The non-volatile memory may include a read-only memory (Read-Only Memory, ROM), a magnetic tape, a floppy disk, a flash memory, an optical memory, and the like. The volatile memory may include a random access memory (Random Access Memory, RAM) or an external cache. For the purpose of description instead of limitation, the RAM is available in a plurality of forms, such as a static RAM (Static Random Access Memory, SRAM) or a dynamic RAM (Dynamic Random Access Memory, DRAM).

In description of this specification, description of reference terms such as "some embodiments", "other embodiments", or "a desirable embodiment", means including specific features, structures, materials, or features described in the embodiment or example in at least one embodiment or example of the present invention. In this specification, schematic descriptions of the foregoing terms do not necessarily point at a same embodiment or example.

The technical features in the foregoing embodiments may be randomly combined. For concise description, not all possible combinations of the technical features in the embodiments are described. However, provided that combinations of the technical features do not conflict with each other, the combinations of the technical features are considered as falling within the scope described in this specification.

The foregoing embodiments only describe several implementations of this application specifically and in detail, but cannot be construed as a limitation to the patent scope of this application. It should be noted that for a person of ordinary skill in the art, several transformations and improvements can be made without departing from the idea of this application. These transformations and improvements belong to the protection scope of this application. Therefore, the protection scope of the patent of this application shall be subject to the appended claims.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

What is claimed is:
1. A control method for a vaporization amount, the control method comprising:
    obtaining a vaporization distance between a vaporization apparatus and a vaporization object;
    before determining a target vaporization power according to the vaporization distance;

obtaining an influence vaporization parameter, the influence vaporization parameter comprising an environmental parameter and/or a vaporization medium type, and selecting a curve corresponding to the influence vaporization parameter from a plurality of to-be-selected curves as a control curve;

using the control curve to determine the target vaporization power according to the vaporization distance, such that, if the vaporization distance is greater than or equal to a first threshold, the target vaporization power comprises a maximum vaporization power of the vaporization apparatus, and if the vaporization distance is less than the first threshold, the target vaporization power is determined according to a positive correlation between the vaporization distance and a vaporization power; and controlling a power of the vaporization apparatus according to the target vaporization power to adjust a vaporization amount of the vaporization apparatus.

2. The control method for a vaporization amount of claim 1, wherein the control curve comprises a first control curve, and the first control curve is as follows:

$$y(x) = \begin{cases} f_1(x), x < D_1 \\ W_{max}, x \ge D_1 \end{cases}$$

wherein x is the vaporization distance, y(x) is the target vaporization power corresponding to the vaporization distance, $D_1$ is the first threshold, $W_{max}$ is the maximum vaporization power, $f_1(x)$ reflects the positive correlation between the vaporization distance and the vaporization power, and a slope of $f_1(x)$ decreases with an increase of the vaporization distance.

3. The control method for a vaporization amount of claim 1, wherein the control curve comprises a second control curve, and the second control curve is as follows:

$$y(x) = \begin{cases} f_2(x), x < D_1 \\ W_{max}, x \ge D_1 \end{cases}$$

wherein x is the vaporization distance, y(x) is the target vaporization power corresponding to the vaporization distance, $D_1$ is the first threshold, $W_{max}$ is the maximum vaporization power, $f_2(x)$ reflects the positive correlation between the vaporization distance and the vaporization power, and a slope of $f_2(x)$ remains unchanged.

4. The control method for a vaporization amount of claim 1, further comprising:

sending a prompt signal if the target vaporization power is the maximum vaporization power.

5. The control method for a vaporization amount of claim 1, wherein controlling the power of the vaporization apparatus according to the target vaporization power further comprises:

turning off the vaporization apparatus if the vaporization distance is greater than the first threshold within a preset duration.

6. The control method for a vaporization amount of claim 1, wherein the vaporization apparatus comprises a vaporization unit and a drive unit, the drive unit is configured to output a drive signal, and the vaporization unit is configured to vaporize a vaporization medium according to the drive signal, and wherein controlling the power of the vaporization apparatus according to the target vaporization power comprises:

outputting a control signal to the drive unit according to the target vaporization power, the control signal being used to adjust the drive signal to adjust a power of the vaporization unit.

7. A vaporization apparatus, comprising:

a vaporization unit configured to vaporize a vaporization medium;

a ranging unit configured to detect a vaporization distance between the vaporization apparatus and a vaporization object;

a controller configured to control a power of the vaporization unit to adjust a vaporization amount of the vaporization apparatus; and a memory and a processor, the memory storing a computer program, and the computer program, when executed by the processor, implementing the control method for a vaporization amount of claim 1.

8. A control apparatus for a vaporization amount, the control apparatus comprising:

a distance obtaining module configured to obtain a vaporization distance between a vaporization apparatus and a vaporization object;

a control curve obtaining module configured to:

obtain an influence vaporization parameter, the influence vaporization parameter comprising an environmental parameter and/or a vaporization medium type, and select a curve corresponding to the influence vaporization parameter from a plurality of to-be-selected curves as a control curve:

a target vaporization power determination module configured to determine the target vaporization power according to the vaporization distance using the control curve, such that if the vaporization distance is greater than or equal to a first threshold, the target vaporization power comprises a maximum vaporization power of the vaporization apparatus, and if the vaporization distance is less than the first threshold, the target vaporization power is determined according to a positive correlation between the vaporization distance and a vaporization power;

and an adjustment module configured to control a power of the vaporization apparatus according to the target vaporization power to adjust a vaporization amount of the vaporization apparatus.

9. A non-transitory computer-readable medium having processor-executable instructions stored thereon, wherein the processor-executable instructions, when executed by one or more processors, facilitate performance of the method of claim 1.

* * * * *